(12) United States Patent
Wilk

(10) Patent No.: US 6,514,077 B1
(45) Date of Patent: Feb. 4, 2003

(54) SONIC DENTAL PLAQUE REMOVER AND ASSOCIATED METHOD

(76) Inventor: Peter J. Wilk, 185 West End Ave., New York, NY (US) 10023

(*) Notice: Subject to any disclaimer, the term of this patent is extended or adjusted under 35 U.S.C. 154(b) by 0 days.

(21) Appl. No.: 09/435,974

(22) Filed: Nov. 8, 1999

(51) Int. Cl.$^7$ .............................................. A61C 15/00
(52) U.S. Cl. ........................ 433/216; 433/119; 433/80
(58) Field of Search ................................ 433/118, 119, 433/216, 80, 116

(56) References Cited

U.S. PATENT DOCUMENTS

| 3,401,690 | A | * | 9/1968 | Martin | 433/216 X |
|---|---|---|---|---|---|
| 3,514,328 | A | * | 5/1970 | Malin | 433/216 |
| 3,541,583 | A | * | 11/1970 | Deuschle | 433/96 |
| 4,071,956 | A | * | 2/1978 | Andress | 433/119 |
| 4,144,646 | A | * | 3/1979 | Takemoto et al. | 433/119 |
| 4,291,017 | A | * | 9/1981 | Beierle et al. | 433/119 X |
| 4,672,953 | A | * | 6/1987 | DiVito | 433/80 X |
| 5,104,315 | A | * | 4/1992 | McKinley | 433/80 |
| 5,531,722 | A | * | 7/1996 | Van Hale | 433/116 X |
| 5,853,290 | A | | 12/1998 | Winston | |
| 5,980,641 | A | * | 11/1999 | Jakubowski | 433/216 X |

* cited by examiner

Primary Examiner—Nicholas D. Lucchesi
(74) Attorney, Agent, or Firm—R. Neil Sudol; Henry Coleman; William Sapone

(57) ABSTRACT

A method for dental plaque removal intended for consumer use comprises filling the mouth with a physiologically acceptable cleaning solution, solvent, or wash, holding such solution in the mouth under voluntary muscular control, thereafter inserting through the lips an elongate acoustically excitable probe forming, under muscular control, a seal with the lips. The probe is energized and a sonic or ultrasonic cleaning action in the mouth removes incipient plaque deposits from the teeth, without the necessity of visiting each tooth individually with a manual or partially automatic mechanical cleaning implement, such as a toothbrush. In an alternative embodiment, fluid fill is provided through a channel in the probe and filling of the mouth is accomplished following insertion. The method may be used in a more general sense to acoustically clean articles in a flexible portable enclosure by means of a portable probe or tool.

2 Claims, 3 Drawing Sheets

SONIC DENTAL PLAQUE REMOVER AND ASSOCIATED METHOD

FIELD OF THE INVENTION

This invention relates to dental hygiene. In particular, this invention relates to home-based methods for the removal of dental plaque.

BACKGROUND OF THE INVENTION

Dental plaque is a thin almost colorless largely bacterial film that accumulates on teeth. The part of the tooth next to the sulcus, or circumferential space or trough between the gum tissue and the crown or root of the tooth, is extremely difficult to keep free of bacterial plaque. If plaque is permitted to accumulate, it will form tartar which is a rough hard material that adheres to teeth. Plaque and tartar buildup constitute the primary cause of periodontal disease. For these reasons it is desirable to have a safe and easy-to-use method of removing plaque at home, between visits to a dental professional.

Tooth brushing is the mainstay of dental therapy, but brushing cannot remove plaque from the tooth surfaces below the gum line or, to a lesser extent, between the teeth above the gum line. To disrupt plaque in this area manually, the patient must floss at least daily. However, compliance with prescribed flossing has been estimated at 3–18% in the United States.

"Sonic" tooth brushes vibrate a bristled head at frequencies between 300 and 500 Hz and are purported to disrupt plaque on nearby inaccessible dental surfaces through vibration. Ultrasonically vibrated devices achieve a similar effect by vibrating at frequencies in excess of 20 kHz. Consumer products do not exist which deliver ultrasonic frequencies directly to oral surfaces and there may be some confusion with the impressive term "ultrasonic" resulting from imprecision in the use of the similar sounding and accurate term "sonic." Consumer model "ultrasonic toothbrushes" typical work by the downstream ultrasonic excitation of a stream of liquid which subsequently impinges on the teeth. It is believed that residual cavitational collapse in the acoustically relaxing fluid contribute to a cleaning action of the impinging stream, which stream may also contain dentifrices.

In contrast to consumer products, true ultrasonic tools have been commercially avaiably to dental professionals for aiding in the removal of tartar deposits, as an alternative to scraping performed by a dental hygienist. Such true ultrasonic tools may cause damage to teeth or gums by misapplication and are unsuitable for consumer use.

Regardless of the mode of action of "sonic" or "ultrasonic" consumer products aiding in the prevention and removal of plaque deposits, such tools, in common with their purely manually actuated counterparts, require proximation of an active tip or working surface to each dental surface to be cleaned. Therefore, while these acoustic or vibratory tools represent an advance in convenience and comfort over manual brushing and flossing in achieving a similar level of oral hygiene and improve compliance in patients who find flossing impalatable, there is further room for improvement in provision of safe, convenient and effective home dental therapies for the prevention and removal of plaque.

In a related technological area, it is known to clean small rigid objects, such as jewelry findings or watch parts, in an ultrasonic bath. While effective, such baths may not be able to accommodate part shapes which, however, do not exceed the volume of the basin or tray. For a given available cleaning volume, the bath devices are also relatively cumbersome to transport, being designed for table-top use in a fixed location. A more flexible sonic or ultrasonic cleaning method and associated device, able to handle a larger variety of parts for a fixed transportable weight and size, would therefore have utility for technicians working outside the lab, in the field.

OBJECTS OF THE INVENTION

It is an object of this invention to provide a method and/or device aiding in the prevention and removal of dental plaque.

It is a further object of this invention to provide such a method and/or device which is usable by a consumer.

In another aspect of the present invention, it is an object to provide a portable cleaning device and/or an associated method able to handle a wider variety of part shapes for a fixed transport weight and size as compared with present ultrasonic parts cleaners.

These and other objects will become apparent through an examination of the drawings and descriptions contained herein.

SUMMARY OF THE INVENTION

As discussed above, existing methods and devices aiding in the removal of dental plaque, whether purely manual or power assisted, require application in the mouth at or near each targeted dental surface in order to be effective. A more efficient, easily used device would be one which processed a broader swath of the mouth at one pass, ideally including the entirety of the inside of the mouth in one cleaning operation. Existing vibratory dental cleaning devices, whether operating in a sonic or an ultrasonic frequency range, remain topical in application. However, in other cleaning applications, it is known to create an ultrasonic bath, i.e., a container enclosing an ultrasonically excitable active volume of cleaning fluid into which a plurality of parts may be inserted for simultaneous cleaning. It is found in such applications, as used for the cleansing of jewelry fittings and other small parts, that the exact placement of the parts in a volume of cleaning fluid is not critical and that parts immersed in many locations in the fluid may be effectively cleaned at the same time. In the prior art, the container is manufactured of a rigid material such as steel and one or more ultrasonic transducers are permanently affixed to the container exemplarily by cement. Ultrasonic vibrations are transmitted from the transducer through the rigid container and into an active fluid volume.

The oral cavity or mouth constitutes a naturally occurring container for the retention of fluid. Furthermore, a physically competent patient may retain a significant volume of fluid in the mouth, substantially filling the space between jaw and palate without excessive swallowing or leakage past the lips. The present invention accordingly recognizes that the oral cavity constitutes a suitable natural enclosure for creating an ultrasonic bath for cleaning of the teeth. The oral cavity is largely lined with at least an integument of soft tissue, as opposed to a rigid surface, and is at least partially variable in overall shape and volume. The volume and shape of the oral cavity is easily modified by an individual by controlling the angle of the jaw and positions of soft tissue processes such as the lips, the tongue, the uvula, the epiglottis, and anterior and posterior structures known as the pillars of the fauces, between which structures passes an orifice known as the isthmus of the fauces, i.e, the throat. The throat and the lips can be closed by voluntary muscular action, rendering the oral cavity a substantially fluid-tight container.

In general, in a novel method of acoustic cleaning in accordance with the present invention, an at least semi-flexible cavity or sack may be filled with a working fluid or solvent and at least one article to be sonically cleaned. An elongate sonic or ultrasonic probe is introduced into the cavity by means of a flexible orifice or embouchure which is subsequently made fluid tight around a shaft of the probe. The probe is activated and an enclosed volume of fluid is acoustically energized, providing a cleaning action of the enclosed article or articles. It is believed, in the case of ultrasonic energization, that the associated cleaning action is attributable to ultrasonic cavitation in the working fluid at a rigid surface. It should be recalled in the context of the present invention that plain water is properly regarded as a solvent.

In a particular application of the present invention to oral hygiene, the semi-flexible cavity may be the human mouth, an elongate sonic probe being inserted past the lips, which form a substantially fluid-tight seal around a shaft of the sonic probe, an additional substantially fluid tight seal being formed by further muscular action at the throat. An energization of the probe is associated with a cleaning action on exposed dental surfaces, and in particular the removal of plaque deposits. The mouth is first filled with a non-toxic cleaning composition or wash, typically but not necessarily by drinking from a cup. Subsequent to the filling, a vibratory probe is inserted past the lips and energized. In a first embodiment of the instant procedure, the probe is held in a fixed location, for example near the center of the mouth, for a present time, much as one would obtain a reading from an oral thermometer. A timer on an ancillary external unit providing a source of vibratory energy to the probe alerts the user when a preset cleaning interval has expired. The deenergized probe is then removed from the mouth, and the cleaning solution expectorated. An optional rinse step may further remove loosened detritus for the mouth.

In a second embodiment of a hygienic procedure in accordance with the instant invention, the probe is actively moved about the mouth by the user during an interval of energization. Vibratory energy may thereby be applied more strongly to nearby teeth, or focussed by the internal geometry of the hard surfaces of the mouth, and thereby, by moving the probe and accommodating the movement by cooperative voluntary movement of the jaw and areas of soft tissue such as the cheeks and tongue, a more uniform cleaning of dental surfaces ultimately achieved. This embodiment represents an intermediate case between dedicated cleaning of each tooth surface by direct mechanical contact, as realized by brushing or flossing, and a single step whole mouth cleaning. It thus still represents a time-saving over detailed mechanical contact, while providing a comparable degree of cleaning.

In another aspect of the present invention, the probe has an operating frequency, and that frequency may be ultrasonic. In a particular embodiment, frequency and energy level may be under user control, either through one of two or more presets, or continuously over a preset range. Thus embodiments may range from a "basic" model, with fixed power level and timing, designed to be inserted in a user's mouth for a preset interval, to "advanced" models, allowing a user to adjust power, frequency and duration, within established preset limits.

DETAILED DESCRIPTION OF THE INVENTION

Figure 1:
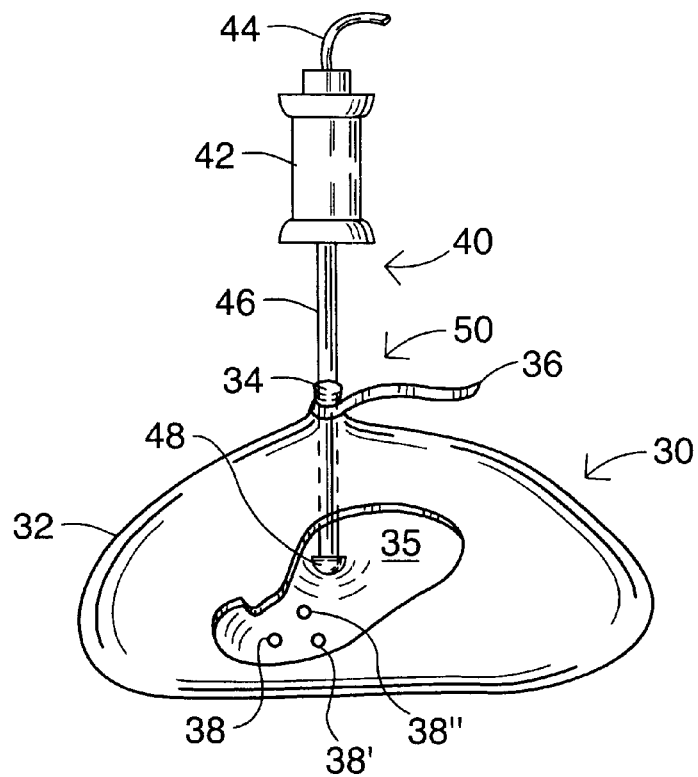
FIG. 1 is partially a schematic perspective view and partially a cut away view of a container adapted for sonic or pressure-wave cleaning in accordance with the present invention.

As illustrated in FIG. 1, a flexible enclosure 30 for acoustically cleaning parts includes a body 32 and a neck 34, the body defining a volume or cavity 35 filled with a working fluid (not separately designated). Enclosure 30 contains articles 38, 38', 38" to be cleaned acoustically. Vibratory probe 40 is inserted through an embouchure or throat 50 formed in neck 34 of enclosure 30. Probe 40 includes a shaft 46, a head 48, a handle 42 and a power cord 44. A substantially fluid tight seal is effected between a shaft 46 of probe 40 and neck 34 by adjustment of a closure device 36, which may take the form of a draw string. Probe 40 is energized by means via power cord 44 to imbue the working fluid with acoustic or vibratory energy and effectuate a cleaning action on exposed surfaces (not designated) of articles 38, 38', 38". Following energization, the probe may be optionally manipulated via handle 42 to bring the probe into successive approximation with a plurality of surfaces.

Figure 2:
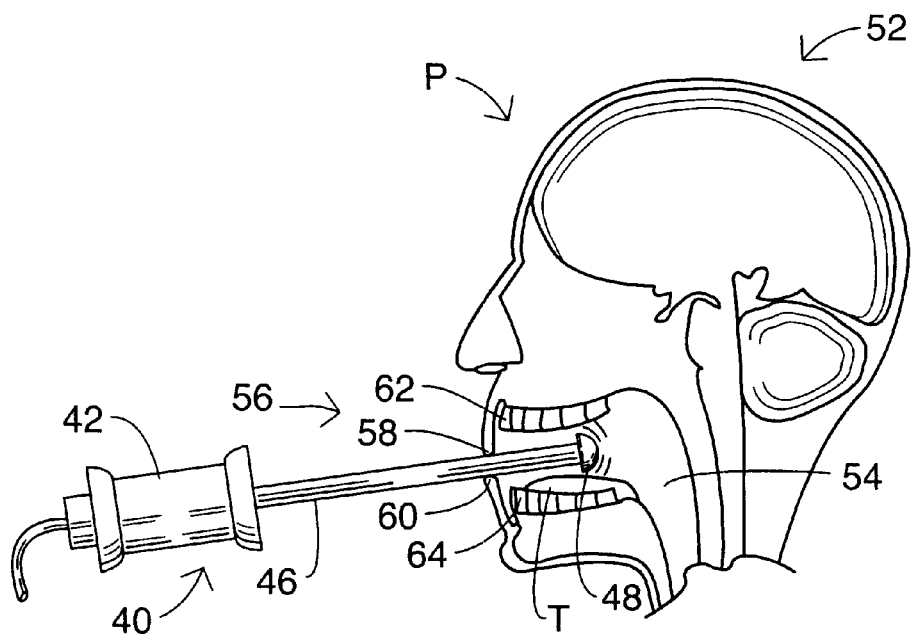
FIG. 2 is partially a cross-sectional view and partially a perspective view of a human user and an ultrasonic probe, showing a step in a dental cleaning operation in accordance with the present invention.

As depicted in FIG. 2, a distal or free end portion of the same probe 40 may be inserted into an oral cavity 54 of a patient or user P. Cavity 54 functions analogously to interior volume 35 of enclosure 30. Lips 58, 60 of patient P perform the function of neck 34 of enclosure 30, the lips being naturally formable into an embouchure or seal 56 about shaft 46 under voluntary control of the patient. The patient may be instructed to hold shaft 46 substantially clear of upper and lower dentation or teeth 62 and 64, respectively. It may be readily seen how the patient is able by manipulation of handle 42 to preferentially subject front or right and left lateral regions (not separately designated) of dentation 62, 64 to acoustic or pressure-wave energy. Individual patients will discover that by movement of soft oral processes, such as tongue T, they may effectively adjust a shape of cavity 54 to preferentially resonantly concentrate acoustic energy on selected areas of dentation.

Alternatively, probe 40 and in particular probe head 48 may be held in an approximately central location (not designated) of oral cavity 54, as shown in FIG. 2, for a pre-selected cleaning interval. The interval is preselected, possibly following consultation with a dentist and optimization for patients with similar jaw size, to provide an acceptable cleaning level to all dental surfaces in a single pass.

Figure 3:
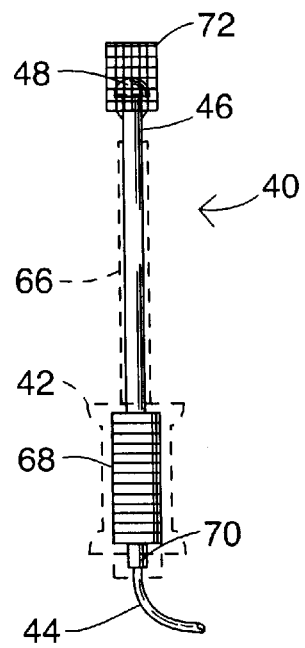
FIG. 3 is a schematic elevational view of an acoustic cleaning probe in accordance with the present invention.

To prevent direct contact between vibrating shaft 46 and teeth 62, 64, probe 40 is optionally provided with a sheath 66, as illustrated in outline in FIG. 3. Sheath 66 allows patient P to comfortably hold probe 40 and in particular probe head 48 in a set position inside oral cavity 54 by clamping shaft 46 with the teeth, as suggested by FIG. 2. Sheath 66 also prevents or minimizes inadvertent contact between vibrating metal surfaces and dental surfaces (not separately designated) where the probe head is moved about inside the mouth or oral cavity during a cleaning or plaque removal operation.

Figure 6:
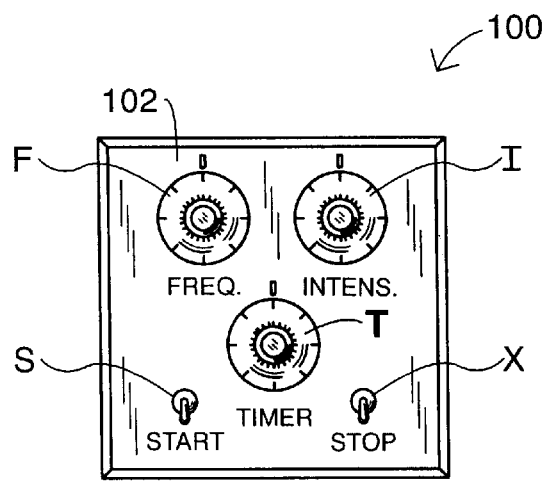
FIG. 6 is a plan view of a faceplate of a power supply controller applicable to the employment of the present invention.

An additional option for enhancing comfort of a user or patient during a dental cleaning operation is the provision of a cage 72, shown in FIG. 3. Cage 72, preferably made of a hard rubber or tough plastic, surrounds probe head 48 and prevents direct contact of dental surfaces or oral mucous membranes (not shown) with the vibrating head. An interior construction of handle 42 is further shown in FIG. 3. Handle 42 contains an electro-acoustic transducer, which may be in the form of a piezoelectric crystal stack 68, coupled to power cord 44 by connector 70. A sonic or ultrasonic excitation signal (not designated) is transmitted or imposed on power cord 44 by standard frequency generator and amplifier circuitry (not shown), well known in the acoustic art, enclosed in a control unit 100 (FIG. 6).

Figure 4:
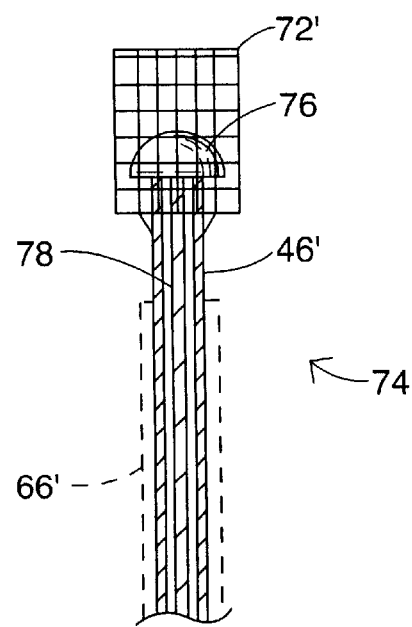
FIG. 4 is partially a plan view and partially a cross-section of an alternative embodiment of an acoustic or ultrasonic cleaning probe in accordance with the present invention.

FIG. 4 depicts a distal probe section 74 of an alternative embodiment of a vibratable probe. A modified tube or shaft 46" mounts an active head or button 76, containing an electro-acoustic transducer (not shown). Wires 78, for energization of the transducer contained in active head 76, pass down a hollow interior (not separately designated) of shaft 46. Wires 78 ultimately are connected to power supply or controller 100. Distal portion of shaft 46' also mounts optional protective screen or cage 72', as well as optional protective sheath 66'. A fluid tight elastomeric seal is provided between button 76 and shaft 46'. Since shaft 46', unlike shaft 46, is not required to transmit acoustic power, and in fact preferentially will not transmit such power, shaft 46' may be manufactured from relatively rigid polymeric organic compounds, such as polyethylene, rather than efficiently acoustically transmitting metals. This material substitution will lessen the need for an elastomeric seal, which may be replaced by simple cement (not shown), and for protective sheath 66'.

Figure 5:
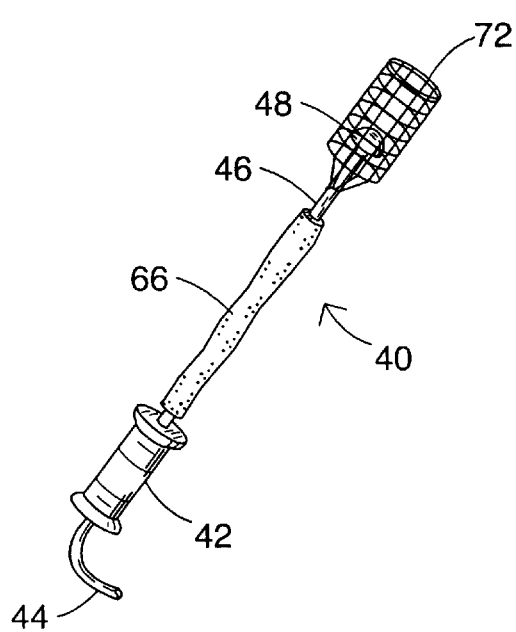
FIG. 5 is a perspective view of the cleaning probe of FIG. 3.

Probe 40 is shown in perspective in FIG. 5 in order to facilitate comprehension of the relation of cage 72, head 48, shaft 46, sheath 66 and handle 42. Probe 74 is similar in external appearance with the exception of sheath 66, which may be eliminated.

Figure 7:
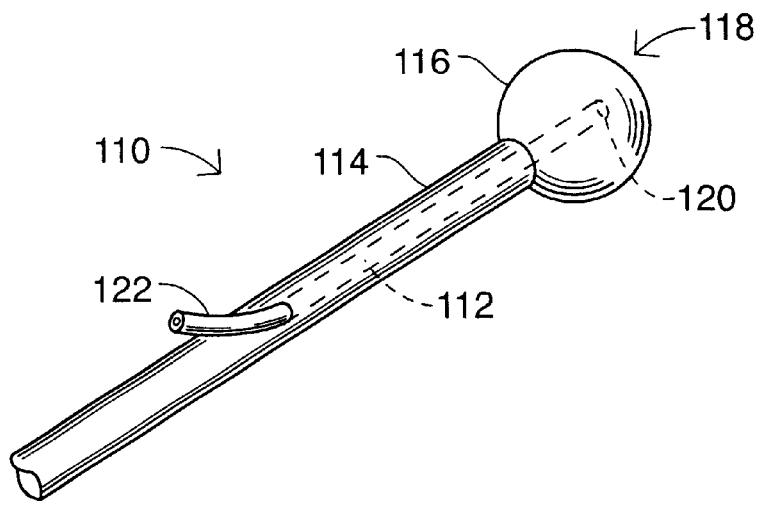
FIG. 7 is aschematic perspective view of an ultrasonic probe in accordance with the present invention.

A further embodiment of an ultrasonic probe, illustrated generally at 110 in FIG. 7, includes a fluid passageway 112 centrally and coaxially located in a shaft 114 of probe 110. Passageway passes through a head 116 at a distal tip 118 of probe 110 and exits at an aperture 120 in the probe head. Passageway 112 extends at least partially along hollow shaft or rod 114 and is connected via an extension 122 with a fluid source (not shown) for enabling a controlled irrigation of the oral cavity on actuation of a control, located for example on a handle, similar to handle 42, or on a foot pedal 144 shown schematically in FIG. 8.

Figure 8:
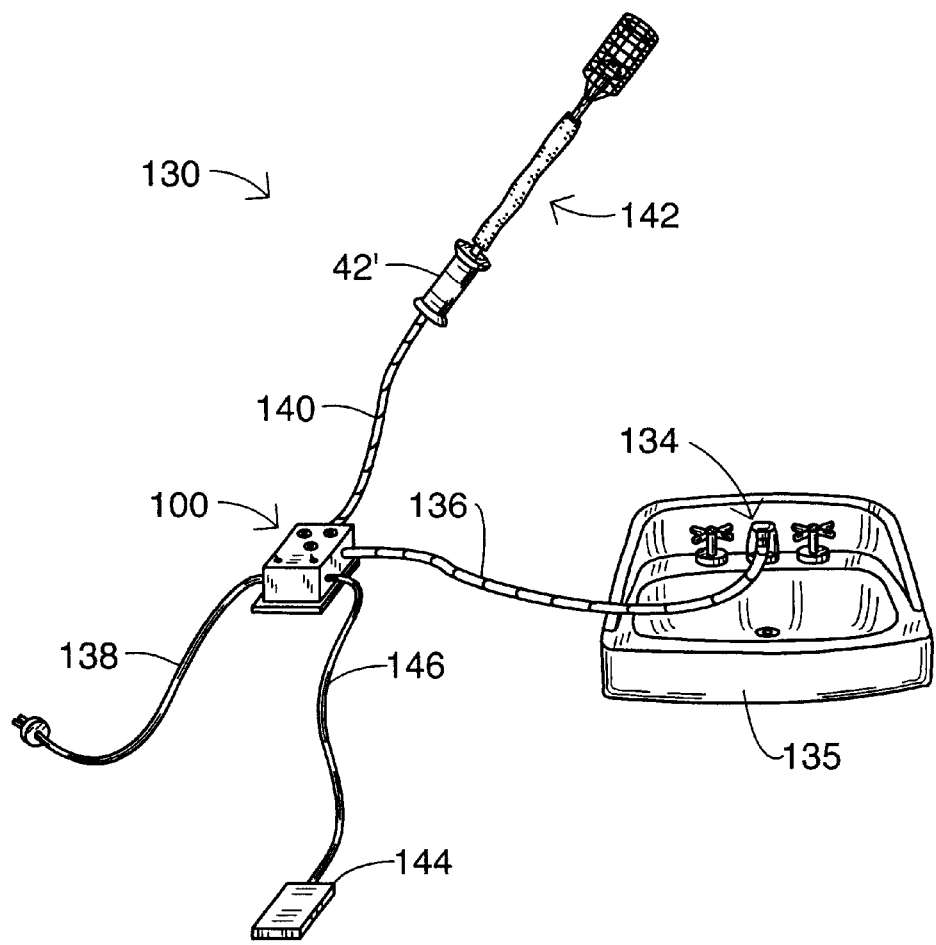
FIG. 8 is a schematic perspective view of an acoustic or ultrasonic cleaning system in accordance with the present invention.

FIG. 8 shows an assembly 130 of components of a complete home dental plaque removal system. A control or power supply box 100 provides a center point or nexus of the system and is weighted and provided with non-skid feet (not shown) for anchoring to an available horizontal bathroom surface such as a toilet tank lid. Control box 100 is connected via a hose 136 to a water supply 134 such as a faucet of a sink 135 and is further connected to a source of line current (not shown) through a line cord 138. An oral irrigator/acoustic probe assembly generally shown at 142 embodies features of probes discussed hereinabove. Probe assembly 142 is connected to control box 100 via a combined power and water supply line 140. Disinfectants, dentifrices or other useful compositions may be optionally combined with water from supply 134, for example, from concentrates (not shown) stored in control box or unit 100. Control of sonic energization of distal tip of probe 142 or irrigation via a passageway or channel is optionally provided by foot pedal 144 which is connected to unit 100 via a cable 146. Functions of pedal 144 may be at least partially user selectable.

In an alternate fluid flow configuration of probe 142, a transducer stack (not illustrated) in handle 42', similar in configuration to stack 68 of handle 42 (FIG.3), may be constructed with a central channel. This channel may be utilized to provide central coaxial flow of a working fluid through the transducer stack.

A faceplate 102 of power supply or control unit 100 is illustrated in FIG. 6. A user may adjust a frequency of acoustic excitation, an intensity level of acoustic excitation, and a timed interval of operation, via manipulation of controls F, I and T respectively. Upon setting of controls F, I, T, the user depresses start button S, which commences a timed cleaning operation at the selected settings. The operation will persist until expiration of the set time or until the user actuates a stop button X to prematurely terminate the operation. Alternatively, timer control or dial T may be adjusted to a "continuous" setting (not shown) for inducing or enabling continuous excitation of an attached acoustic probe until stop button X is depressed. The illustrated controls represent a "high end" device and certain simplifications are possible, down to eliminating all controls with the exception of timer T and start and stop buttons S, X. Elimination of timer control T is also possible so that the device is controlled only by "on/off" switches S, X, at a factory set nominal operating frequency and intensity.

Although the invention has been described in terms of particular embodiments and applications, one of ordinary skill in the art, in light of this teaching, can generate additional embodiments and modifications without departing from the spirit of or exceeding the scope of the claimed invention. It is to be recognized that controls shown are for illustrative purposes, and different control styles and more elaborate functionality may be incorporated without violating the spirit of the current invention. For example, a technically sophisticated user may with to experiment with various acoustic waveforms, such as square, saw tooth, pure sinusoidal, etc. Waveform and other controls could be integrated into a single multifunction graphical display and data entry pad. A foot pedal could be conveniently employed for on/off functionality, and, tending towards simplicity rather than complexity, all control functions could be reduced to foot pedal actuation of a unit working at factory preset frequency and power.

Accordingly, it is to be understood that the drawings and descriptions herein are proffered by way of example to facilitate comprehension of the invention and should not be construed to limit the scope thereof.

What is claimed:
1. A method for cleaning surfaces inside a cavity, comprising:
   providing a vibratably excitable probe having a shaft and a sheath disposed about said shaft;
   inserting said probe into a cavity through an orifice so that a boundary surface defining said orifice engages said sheath is isolated or spaced from said shaft;

providing a working fluid in said cavity, said probe having a working tip disposed in said working fluid; and exciting said probe in vibration, causing a cleaning action to be transmitted through said working fluid to a surface contained in said cavity and at least partially covered by said fluid, the boundary surface of said orifice being protected from direct contact with said shaft by said sheath.

2. A method for cleaning surfaces inside a cavity, comprising:

providing a vibratably excitable probe having a working tip surrounded by a cage;

inserting said working tip and said cage into a cavity through an orifice;

providing a working fluid in said cavity, said working tip and at least a portion of said cage being disposed in said working fluid;

exciting said probe in vibration, causing a cleaning action to be transmitted through said working fluid to a surface contained in said cavity and at least partially covered by said fluid; and moving said probe so that said working tip and said cage are disposed at different locations in said cavity during exciting of said probe, said cage protecting surfaces in said cavity from direct contact with said working tip.

* * * * *